United States Patent [19]
Samuel et al.

[11] Patent Number: 5,552,144
[45] Date of Patent: Sep. 3, 1996

[54] IMMUNOGENIC SHIGA-LIKE TOXIN II VARIANT MUTANTS

[75] Inventors: James E. Samuel, Germantown; Valery M. Gordon, Kensington, both of Md.

[73] Assignees: MicroCarb, Inc., Gaithersburg, Md.; The United States of America as represented by the Secretary of the Army, Washington, D.C.

[21] Appl. No.: 180,761

[22] Filed: Jan. 10, 1994

Related U.S. Application Data

[63] Continuation of Ser. No. 824,139, Jan. 22, 1992, abandoned.
[51] Int. Cl.$^6$ .......................... A61K 39/108; C07K 14/25; C07K 14/245; C12N 9/24
[52] U.S. Cl. ..................... 424/236.1; 424/241.1; 530/350; 530/825; 435/200
[58] Field of Search .................... 424/92, 236.1, 424/241.1; 530/350, 825; 435/69.1, 200

[56] References Cited

U.S. PATENT DOCUMENTS

| | | | |
|---|---|---|---|
| 4,136,181 | 1/1979 | Dobrescu et al. | 424/92 |
| 4,632,830 | 12/1986 | Formal et al. | 424/93 A |
| 4,950,740 | 8/1990 | Greenfield et al. | 514/2 |

OTHER PUBLICATIONS

Yamasaki et al, "Analysis of Structure–Function Relationship of Vero Toxin 1(VT1) . . . ", *Japan J. Med. Sci Biol.* 42:180 (Oct.–Dec. 1989).

Head et al "Serological Differences Between Verocytotoxin 2 And Shiga–Like Toxin II", *The Lancet* (II):751 (Sep. 1988).

"Schulz et al, *Principles of Protein Structure*", pp. 14–16, Springer–Verlag (NY) 1979.

Gyles et al, "Cloning and Nucleotide sequence analysis of the genes determining verocytotoxin . . . " *Microb. Pathog.* 5:419–426 (1988).

Jackson et al, "Mutational Analysis of the Shiga Toxin . . ." *J. Bacter.* 172(6): 3346–3350 (Jun. 1990).

Yamasaki et al, "Importance of arginine at position 170 . . . " *Microb. Pathog.* 11(1): 1–9, abstract only (Jul. 1991).

Gyles et al, "Cloning and nucleotide sequence analysis . . . ", *Chem. Abst.* 110:181, Abst#186,883h (Feb. 1989).

Frankel et al, "Selection and Characterization of Ricin Toxin A–Chain . . . " *Mol. Cell. Biol.* 9(2); 415–420 (Feb. 1989).

Weinstein et al, "Cloning and Sequencing of a Shiga–Like Toxin Type II . . . " *J. Bacter.* 170(9): 4223–4230 (Sep. 1988).

Hovde et al, "Evidence that glutamic acid 167 is an active site residue . . . " *PNAS* 85: 2568–2572 (Apr. 1988).

Samuel et al, "Comparison of the Glycoliped Receptor . . . " *Inf. Immun.* 58: 611–618 (Mar. 1990).

Ito et al, "Cloning and nucleotide sequencing of Vero toxin 2 . . . " *Microb. Pathog.* 8: 47–60 (1990).

Jackson et al., "Mutational Analysis of the Shiga Toxin . . . ", *J. Bacter.* 172(6): 3346–3350, Jun. 1990.

Yamasaki et al., "Importance of arginine at position 170 . . .", *Microb. Pathog.* 11(1): 1–9, Jul. 1991, abstract only.

Gyles et al., "Cloning and nucleotide sequence analysis . . .", *Microb. Pathog.* 5(6): 419–26, 1988, abstracted in *Chem. Abst.* 110: 181, Abst. #186883h, Feb. 22, 1989.

(List continued on next page.)

*Primary Examiner*—Stephen G. Walsh
*Attorney, Agent, or Firm*—Pennie & Edmonds

[57] ABSTRACT

Disclosed herein are immunogenic mutant Shiga-Like Toxin II variants and vaccines containing such toxins. The mutant toxin comprises an SLT-IIv where the amino acid at position 167 in the A subunit has been replaced by a differently charged amino acid that essentially maintains the structure of the native A subunit. In a preferred embodiment, the glutamic acid is replaced with glutamine. An analogous modification may also be made at position 170. The vaccines are used for edema disease of swine.

6 Claims, 6 Drawing Sheets

OTHER PUBLICATIONS

Frankel et al., *Mol. Cell. Biol.* 9(2): 415–420, Feb. 1989.

Schulz et al., *Principle of Protein Structure,* pp. 14–16, 1979.

Schlossman et al., Molecular and Cellular Biology, 9(11):5012–5021 (1989).

MacLeod et al., Veterinary Microbiology, vol. 29:309–318 (1991).

Gordon et al, "An Enzymatic Mutant of Shiga–like Toxin II Variant is a Vaccine Candidate for Edema Disease of Swine," *Abstracts Twenty–Seventh Joint Conference on Cholera and Related Diarrheal Diseases,* 149–152 (1991).

IMMUNOGENIC SHIGA-LIKE TOXIN II VARIANT MUTANTS

This is a continuation of application Ser. No. 07/824,139, filed Jan. 22, 1992, now abandoned.

FIELD OF THE INVENTION

This invention relates to bacterial toxins and, in particular, to a mutant Shiga-Like Toxin II variant (SLT-IIv). The mutant toxin may be used in a vaccine against SLT-IIv-producing bacteria and as an adjuvant in vaccines containing immunogens against other disease-producing microorganisms.

REFERENCES

Several publications are referenced herein by Arabic numerals within parenthesis. Full citations for these references may be found at the end of the specification immediately preceding the claims. The disclosures of these publications are hereby incorporated herein by reference in their entirety unless otherwise noted.

BACKGROUND OF THE INVENTION

*Shigella dysenteriae* type 1 and strains of *Escherichia coli* which produce, respectively, the protein exotoxins Shiga toxin and Shiga-like toxins are responsible for a variety of diseases in humans and animals. In humans, toxin-producing bacteria cause colonic disease which may progress to hemorrhagic colitis (15, 17) and serious extraintestinal sequelae, including thrombotic thrombocytopenic purpura (18) and the hemolytic uremic syndrome (11, 15). Weaned pigs infected with *E. coli* producing Shiga-like toxin II variant (SLT-IIv) develop edema disease (ED), a disorder characterized by profound generalized vascular damage, edema in subcutaneous and gastrointestinal tissues, neurological abnormalities, and death (2, 16).

Strains of *E. coli* that cause ED are included within a limited number of serogroups, identified as 0138, 0139, and 0141 (10). These strains can produce several proteins which may act as virulence factors in vivo, including heat-labile enterotoxin, heat-stable enterotoxin, hemolysin, and SLT-IIv. Recently, MacLeod et al. reported that intravenous injection of pigs with purified SLT-IIv at doses as low as 1.5 ng/kg of body weight resulted in the development of lesions which are characteristic of ED (14). Therefore, despite the presence of other putative virulence factors in ED isolates, intoxication with SLT-IIv appears to account for the majority of signs seen in ED.

All members of the Shiga-like toxin family are holotoxins, composed of a single A subunit (32.2 kDa) in noncovalent association with a pentamer of B subunits (7.7 kDa) (20, 21). Enzymatic activity resides in the A subunit, and binding activity is conferred by the B subunit. The A subunit is a specific N-glycosidase which cleaves a single adenine from the 28S rRNA component of eukaryotic ribosomes (3). This action results in an inhibition of protein synthesis.

Although antigenically similar to SLT-II (16), SLT-IIv is classified as a variant because it has reduced toxicity for HeLa cells, whereas SLT-II is equally toxic to both Vero and HeLa cells (16). This differential cytotoxicity may be explained, in part, by a difference in eukaryotic receptor binding. Although both toxins bind glycolipid of the globo-series, SLT-IIv appears to preferentially bind globotetraosylceramide ($Gb_4$), while SLT-II and other members of the Shiga-like toxin family primarily bind globotriaosylceramide ($Gb_3$) on the target cell surface (22). The nucleotide sequence and the deduced amino acid sequence for the A and B subunits of SLT-IIv are known (26).

Currently, there are no effective vaccines against ED. Using oligonucleotide-specific site-directed mutagenesis, we have identified amino acid changes in the A subunit that drastically reduce the enzymatic activity of SLT-IIv. Such a mutagenized SLT-IIv represents a suitable candidate for a vaccine against ED.

SUMMARY OF THE INVENTION

It is an object of the invention to provide an immunogenic mutant SLT-IIv 3 as described by SEQ ID NO's 1–3 on pages 30–33.

Another object of the invention is to provide an immunogenic polypeptide comprising a mutant A subunit of SLV-IIv as described by SEQ ID NO. 1–2 on pages 30–32.

A further object of the invention is to provide methods and vaccines for inducing an immune response in an animal host to bacteria that cause edema disease of swine.

Additional objects and advantages of the invention will be set forth in part in the description that follows, and in part will be obvious from the description, or may be learned by the practice of the invention. The objects and advantages of the invention will be attained by means of the instrumentalities and combinations particularly pointed out in the appended claims.

To achieve the objects and in accordance with the purpose of the invention, as embodied and properly described herein, the present invention provides an immunogenic mutant SLT-IIv where the amino acid at position 167 in the A subunit has been replaced by a differently charged amino acid that essentially maintains the structure of the native A subunit in the mutant toxin. Preferably, the glutamic acid at position 167 is replaced by glutamine. The mutated toxin is preferably used as a vaccine against swine edema disease. An immunologically effective amount of the toxin, preferably in a pharmaceutically acceptable carrier, is administered to an animal host, preferably a pig. In an alternative embodiment, the mutant SLT-IIv is used as an adjuvant in a vaccine against other illnesses caused in humans or animals by microorganisms.

The accompanying drawings, which are incorporated in and constitute a part of this specification, illustrate one embodiment of the invention and, together with the description, serve to explain the principles of the invention.

BRIEF DESCRIPTION OF THE DRAWINGS

FIG. 1A: Purified SLT-IIv toxoid or SLT-IIv toxin (1.5 micrograms) was separated by PAGE. Proteins were transferred to nitrocellulose and incubated with bovine polyclonal monospecific antisera raised against purified SLT-IIv. FIG. 1B Purified SLT-IIv toxoid or SLT-IIv toxin (1.5 micrograms) was separated by SDS-PAGE, and the proteins were visualized by silver staining. Lanes 1, SLT-IIv toxoid; lanes 2, SLT-IIv toxin. Prestained molecular weight standards are in the rightmost lane of panel A; molecular weights (in thousands) are shown on the right.

FIG. 3 shows inhibition of protein synthesis by SLT-IIv toxin and SLT-IIv toxoid. Aliquots of rabbit reticulocyte lysate (35 microliters) were incubated with various concentrations of purified SLT-IIv toxin (●) or SLT-IIv toxoid (▲). Lysates were then assayed for protein synthesis as compared with control lysates to which no toxin was added. These results represent the means from three or more experiments.

FIG. 4 shows inhibition of protein synthesis by purified SLT-IIv and purified SLT-IIv mutants. ●, SLT-IIv; ▼, SLT-IIvR170K; ■, SLT-IIvE167D; ▲, SLT-IIvE167D/R170K; ♦, SLT-IIvE167Q. These results represent the means from three or more experiments.

DETAILED DESCRIPTION OF THE INVENTION

Figure 1A:
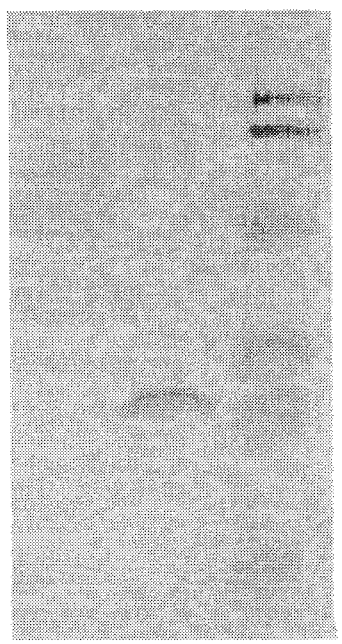
FIG. 1A and FIG. 1B show immunoblot and SDS-PAGE comparing formaldehyde-treated and native SLT-IIv.

Reference will now be made in detail to the presently preferred embodiments of the invention, which, together with the following example, serve to explain the principles of the invention.

The invention relates to a mutant SLT-IIv whose enzymatic activity and cytotoxicity are significantly reduced compared to the wild-type toxin. In this mutant, the amino acid at position 167 in the A subunit has been replaced by a differently charged amino acid that essentially maintains the structure of the native A subunit in the mutant. As used herein, the term "differently charged amino acid" means that the side chain (R group) on the amino acid has gone from negatively charged to positively charged or vice versa or polar to nonpolar or vice versa or polar to negatively charged or positively charged or vice versa. That is, a charge switch has occurred. As also used herein, the term "structure" refers particularly to the secondary and tertiary structure, relating to the folding of the polypeptide, and the quaternary structure, relating to the assembly of the holotoxin. It is particularly important that the mutated A subunit polypeptide be able to be assembled with the native B subunit polypeptide to produce the complete holotoxin. If the structure is essentially maintained, i.e., if the mutant A polypeptide is able to fold in essentially or substantially the same configuration as the native A subunit polypeptide and if the mutant polypeptide is able to assemble with the native B subunit polypeptides to produce the holotoxin, then the resulting toxin will be immunogenic, yet have a greatly reduced enzymatic activity and cytotoxicity.

Preferably, the mutant toxin contains an A subunit in which the amino acid at position 167 is glutamine instead of glutamic acid. The enzymatic activity of this toxin is reduced by at least about 1,500-fold when compared to the native SLT-IIv toxin. It also has a reduction in cytotoxicity of at least about $10^6$-fold when compared to the native toxin.

The invention also comprises mutant toxins where the amino acid at position 170 in the A subunit has also been replaced by a differently charged amino acid that essentially maintains the structure of the native A subunit in the mutant. This substitution results in a further reduction in enzymatic activity and cytotoxicity. Preferably, the arginine at position 170 is replaced by glutamine.

The mutant toxins of the invention are prepared by site-directed mutagenesis. Such techniques are well known in the art and can be readily applied by persons skilled in the art to the preparation of the toxins in the invention, in view of the teachings contained herein. In general, DNA, which encodes the expression of the wild-type A subunit polypeptide, is placed into a plasmid, which is transformed into a compatible microorganism, such as E. coli. Single-stranded DNA is isolated by standard techniques. This provides a template for hybridization with a mutagenizing oligonucleotide prepared by standard techniques. Preferably, such oligonucleotide is about 20 nucleotides in length. It is the same as the related wild-type DNA, except for the single desired change in the one to three base pairs. The oligonucleotide and the single-stranded DNA are then caused to form double-stranded DNA, which is further manipulated by known techniques, whereby the original strand is degraded and a new one complementary to the oligonucleotide is synthesized. The new DNA is cloned into an appropriate host, and the mutated A subunit polypeptide is produced. This DNA is further cloned in conjunction with the DNA for the B subunit into an appropriate host so that the mutant toxin of the invention is produced.

This method allows the mutant subunit A polypeptide to be produced separately. The mutant subunit A polypeptide is also expected to be immunogenic and to have a greatly reduced enzymatic activity. Accordingly, it also could be used as a vaccine, although the mutant holotoxin itself is preferred.

Since the preferred use of the mutant toxins and polypeptides is as an immunogen in a vaccine, the toxins and polypeptides are preferably purified. They are essentially pure, i.e., purified to greater then 95% homogeneity, as determined by SDS-PAGE.

The mutant toxins and polypeptides of the invention may be used in vaccines for inducing an immune response in an animal host to the bacteria that cause edema disease of swine, thus preventing, ameliorating, or treating the disease. Preferably, the animal host is a pig, and most preferably it is a suckling pig.

The vaccines comprise an immunologically effective amount of the immunogen in a pharmaceutically acceptable carrier. The combined immunogen and carrier may be an aqueous solution, emulsion, or suspension. An immunologically effective amount is determinable by means known in the art without undue experimentation, given the teachings contained herein. In general, the quantity of immunogen will be between 1 and 50 micrograms per dose. Preferably, multiple doses are given. The carriers are known to those skilled in the art and include stabilizers, diluents, and buffers. Suitable stabilizers include carbohydrates, such as sorbitol, lactose, manitol, starch, sucrose, dextran, and glucose and proteins, such as albumin or casein. Suitable dilutents include saline, Hanks Balanced Salts, and Ringers solution. Suitable buffers include an alkali metal phosphate, an alkali metal carbonate, or an alkaline earth metal carbonate.

The vaccine may also contain one or more adjuvants to improve immunogenicity. Suitable adjuvants include aluminum hydroxide, aluminum phosphate, or aluminum oxide or a composition that consists of a mineral oil, such as Marcol 52, or a vegetable oil and one or more emulsifying agents.

The vaccines of the invention are prepared by techniques known to those skilled in the art, given the teachings contained herein. Generally, the immunogens are mixed with the carrier to form a solution, suspension, or emulsion. One or more of the additives discussed above may be in the carrier or may be added subsequently. The vaccine preparations may be dessicated, for example, by freeze drying for storage purposes. If so, they may be subsequently reconstituted into liquid vaccines by the addition of an appropriate liquid carrier.

The vaccines may be administered by known routes of administration for this type of vaccine. The preferred routes are subcutaneous or intramuscular injection.

Accordingly, the invention also comprises a method for inducing an immune response to SLT-IIv producing bacteria in a mammal in order to protect the mammal against the effects of the toxin. The method comprises administering an immunologically effective amount of an immunogen of the invention to the host and, preferably, administering a vaccine of the invention to the host.

The mutant toxins and polypeptides of the invention may also be used as adjuvants in vaccines against various types of microorganisms, including those that produce diseases in humans. For example, a currently marketed vaccine against *Haemophilus influenza* type b comprises fragments of the polysaccharide coat of the bacterium conjugated to diptheria toxin. A second example uses cholera toxin A and/or B subunits for adjuvant activity coupled to surface proteins from bacteria causing disease unrelated to disease caused by *Vibrio cholerae*.

The toxins and polypeptides of the invention are also useful as reagents for scientific research on the properties of pathogenicity, virulence, and infectivity of SLT-IIv producing bacteria, as well host defense mechanisms. A composition in accordance with the present invention useful as an investigational reagent contains an amount of the mutant toxin or polypeptide effective to provide the information or analysis sought. The determination of the amount necessary to accomplish a particular research goal depends upon the specific type of investigation involved as is readily within the routine skill of one engaged in such a research.

It is to be understood that the application of the teachings of the present invention to a specific problem or environment will be in the capability of one having ordinary skill in the art in light of the teachings contained herein. Examples of the products of the present invention and processes for their preparation and use appear in the following example.

EXAMPLE 1

Preparation of an Enzymatic Mutant to SLT-IIv
Materials and Methods

Abbreviations

Abbreviations used are as follows: Glc, glucose; Gal, galactose; GalNac, N-acetylgalactosamine; Cer, ceramide; $Gb_2$, Gal(alpha)1-4Gal(beta)1-1Cer; $Gb_3$, Gal (alpha)1-4(beta)1-4Glc(beta)1-1Cer; $Gb_4$, GalNac(beta)1-3Gal(alpha)1-4Gal(beta)1-4Glc(beta)1-1Cer; PBS, phosphate-buffered saline; BSA, bovine serum albumin; SDS-PAGE, sodium dodecyl sulfate-polyacrylamide gel electrophoresis; TLC, thin-layer chromatography; $CD_{50}$, 50% cytotoxic dose; and $ID_{50}$, 50% inhibitory dose.

Bacterial Strains, Plasmids, and Site-Directed Mutagenesis

The wild-type and mutant toxins used in this study were produced by *E. coli* DH5(alpha) transformed with pJES101 (22), which contains the slt-IIv genes expressed under the control of the (beta)-galactosidase promoter in pKS(−) (Stratagene, La Jolla, Calif.). Clones producing high levels of cytotoxic activity were maintained under BL3+EK1 containment. Mutagenesis of the SLT-IIv A-subunit gene was performed in pJES106, an EcoRI-PstI fragment of the toxin genes in pKS(−). The mutagenesis procedure involved transforming pJES106 into CJ236 (dut ung), and uracil-containing single-stranded DNA was isolated by transfection with the helper phage R408. Mutagenizing oligonucleotide primers were synthesized (model 391 PCR-Mate; Applied Biosystems, Inc., Foster City, Calif.) and were used to initiate plasmid replication, and mutagenized plasmids were purified from MV1190 ($dut^{35}$ $ung^{\pm}$). Mutations were confirmed by double-stranded sequencing (Sequenase; USB, Cleveland, Ohio). Holotoxin production was restored by cloning the mutagenized EcoRI-PstI fragment into pJES101, and each mutation was confirmed by a second sequence analysis.

Toxin Production and Purification

The Shiga-like toxin preparations used in this study were either crude sonicates or purified toxins. To obtain the crude sonicate, a 6-ml culture of toxin-producing bacteria was grown overnight in the presence of 200 micrograms of ampicillin per ml and the total culture was sonicated and clarified by centrigugation at 10,000×g for 15 min. To obtain purified toxin, a 1-liter culture was grown for 24 h and the supernatant was used as a source of toxin. This material was concentrated with 60% ammonium sulfate and subjected to ion-exchange chromatography, as has been previously described (22). This preparation was essentially pure, as determined by SDS-PAGE (13).

SDS-PAGE and Immunoblots

Proteins were separated on 12% polyacrylamide gels under either reducing or nonreducing conditions and detected by silver stain (Bio-Rad, Richmond, Calif.). Proteins were immunoblotted according to the method of Towbin et al. (25). The toxin subunits were visualized with polyclonal, monospecific bovine sera followed by horseradish peroxidase-conjugated sheep anti-bovine antibody.

The experiments reported here were conducted according to the principles set forth in the *Guide for the Care and Use of Laboratory Animals* (19).

TLC Assay for Toxin Assembly

Purified glycolipids and lipid extracts from sensitive (Vero) and less sensitive (HeLa) cells were separated by TLC as has been previously described (22). Lysates of sonically disrupted bacteria were overlaid on the TLC plates. Bound toxin was detected with 11E10, an anti-SLT-II A-subunit monoclonal antibody. Because the SLT-IIv B subunit recognizes the glycolipid receptor, detection of toxin binding with a monoclonal antibody specifically directed against the A subunit is evidence for association between the A and B subunits.

Injection of Pigs with SLT-IIv Toxoid

Purified toxin was chemically modified by treatment with 1% formaldehyde at 37° C. for 24 h and then dialyzed extensively against PBS, pH 7.4. Sixty-eight pigs from eight litters were divided into two groups and were vaccinated with Al(OH)$_3$ adjuvant or adjuvant plus toxoid (50 micrograms) subcutaneously on the 7th and 14th days of life. The two groups of pigs were housed in separate buildings. The pigs were weighed on the 22nd, 29th, and 36th days of life.

Determination of Cytotoxicity (CD50) and Neutralizing Antibody Titer of SLT-IIv

The $CD_{50}$ for Vero cells was determined according to the method of Gentry and Dalrymple (7). Briefly, $10^4$ Vero cells were plated in each well of a 96-well microtiter plate (Costar) and dilutions of a control or unknown toxin were applied to the cells. The plates were incubated in an atmosphere of 6% $CO_2$ for 48 h, then fixed with formalin, and stained with crystal violet. The plates were read on a Titertek Multiskan plate reader (Flow Laboratories, McLean, Va.) with a 620-nm-pore-size filter. The titer of the toxin was determined to be the log of the dilution which killed approximately 50% of the cells. For determinations of neutralizing antibody titer, serial twofold dilutions of sera were incubated with two Vero $CD_{50}$ of SLT-IIv. These preparations were then added to Vero cells and further incubated for 48 h at 37° C. The plates were fixed and stained as described above, and the neutralizing antibody titer was expressed as the dilution of antibody which protected the cells from the cytotoxic effect of the toxin.

Assay for Enzymatic Activity of Mutant and Wild-Type Toxins

The enzymatic activity of purified toxins was assayed with an in vitro translation kit (Promega Biotec, Madison, Wis.). Triplicate samples containing 5 microliters of purified toxin in PBS and 35 microliters of rabbit reticulocyte lysate were incubated at 37° C. for 30 min to inactivate the ribosomes. A reaction mixture containing 20 micro-Ci of [$^{35}$S]methionine (NEN Research Products, Wilmington, Del.), 200 ng of brome mosaic virus mRNA, 1 nmol of amino acid mixture minus methionine, and diethyl pyrocarbonate-treated water was added to a final volume of 50 microliters. The mixture was incubated at 30° C. for 20 min. Radiolabeled proteins were precipitated and harvested according to the manufacturer's instructions, samples were counted in a scintillation counter, and results were expressed as percentage of PBS control values. The $ID_{50}$ was determined to be the concentration of toxin which inhibited incorporation of $^{35}$S-methionine by 50%.

Injection of Pigs with SLT-IIvE167Q

Ten pigs from two litters that were born 2 days apart were divided into two groups. For each treatment in the protocol, 2 days were recorded for the ages of the pigs because each group contained pigs from both litters. Five pigs were injected subcutaneously with Al(OH)$_3$ adjuvant containing 50 micrograms of BSA or adjuvant containing 50 micrograms of SLT-IIv containing a mutation of E-167 to Q (SLT-IIvE167Q) on day 17/19 and day 24/26 of life. The pigs were weighed on days 17/19, 24/26, 31/33, and 38/40. Blood samples were obtained from the pigs prior to the first injection and on day 38/40. The pigs were sacrificed on day 38/40, and tissue samples were taken for histological examinations (12).

RESULTS

SLT-IIv shares several regions of sequence homology which ricin, Shiga toxin, and other members of the family of Shiga-like toxins (8, 9). Several amino acids have been implicated by other researchers as playing an important role in enzymatic activity (5, 6, 8, 9). These include glutamic acid at position 167 and arginine at position 170. These two amino acid residues were selected for mutation with a goal of finding a mutated toxin that is significantly reduced in enzymatic activity and is protective against ED.

Figure 1B:
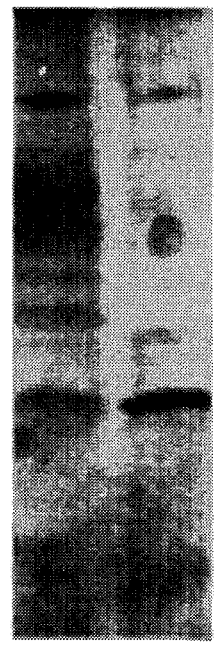
Figure 2A:
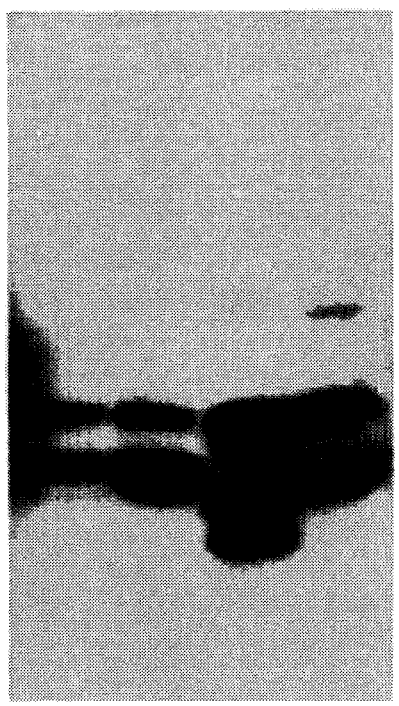
FIG. 2A and FIG. 2B show binding of SLT-IIv toxin and SLT-IIv toxoid to glycolipids separated by TLC. Crude sonicate of toxoid or toxin diluted 1:100 was overlaid onto TLC plates. Glycolipids were visualized by autoradiography after binding to SLT-IIv toxin (FIG. 2A) or SLT-IIv toxoid (FIG. 2B). Lanes 1 and 2, 1 microgram each of $Gb_3$ and $Gb_4$; lanes 3, Vero cell glycolipids from 10 mg of cells; lanes 4, HeLa cell glycolipids from 10 mg of cells.
Figure 2B:
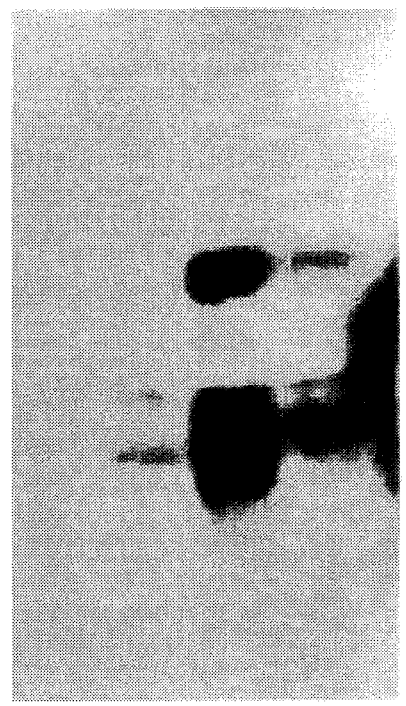

Characterization and Efficacy of a Chemically Cross-Linked Toxoid as an ED Vaccine An initial study was undertaken to determine whether SLT-IIv toxoid would protect pigs from an oral challenge with ED strain S1191. Purified SLT-IIv was chemically modified by treatment with formaldehyde as described in Materials and Methods. This toxoid (FIG. 1, lanes 1 in panel A and B) was then compared with native SLT-IIv (FIG. 1, lanes 2 in panels A and B) by immunoblot (FIG. 1 panel A) and by PAGE (FIG. 1, panel B). The A subunit of the native toxin appeared as a faint band at ~33 kDa, and the $A_1$ polypeptide (~28 kDa) stained more intensely (FIG. 1, lanes 2 in panels A and B). The toxoid (FIG. 1B, lane 1 in panel B) appears to have become extensively cross-linked, resulting in the presence of new immunoreactive higher-molecular-weight species (FIG. 1A, lane 1 in panel A).

Figure 3:
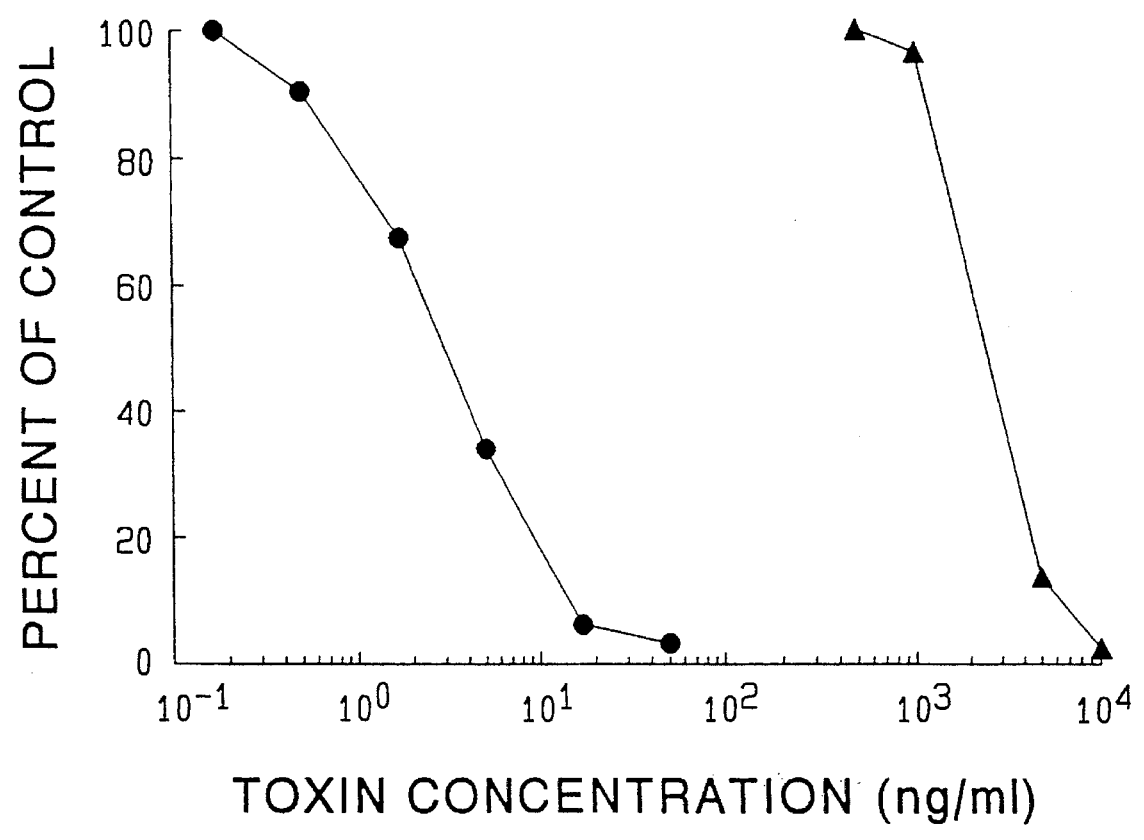

The toxoid and native toxin were compared by a TLC assay to examine the effects of formaldehyde treatment on subunit assembly and receptor recognition. Purified glycolipids and total lipid extracts from sensitive cells (Vero) were separated by TLC. The plates were exposed to purified toxin or toxoid followed by 11E10, a monoclonal antibody that reacts with the A subunit of SLT-IIv. After the addition of $^{125}$I-labeled secondary antibody, the plates were subjected to autoradiography. FIG. 3 panel A shows the pattern obtained with native toxin, and FIG. 3 panel B shows the corresponding pattern obtained with toxoid. The toxoid was reduced in its ability to bind $Gb_4$ and $Gb_3$ but appeared to bind more strongly to $Gb_2$ in sensitive cells (Vero cells; panel B lane 3) and relatively insensitive cells (HeLa cells; panel B lane 4) than did the native toxin (panel A, lanes 3 and 4). The toxoid had no detectable cytotoxic activity as assessed on Vero cell assays (data not shown). Therefore, this toxoid was considered safe for use as a vaccine.

The toxoid preparation was tested for safety and immunogenicity in pigs. Pigs were injected subcutaneously with either 50 micrograms of toxoid in Al(OH)$_3$ adjuvant or PBS and adjuvant on days 5 and 13 of life. Pigs were weighed at intervals in order to monitor the effects of the vaccine. As shown in Table 1, there were significant weight differences between pigs that had been vaccinated with the toxoid and those that were injected with adjuvant alone. Pigs that were exposed to the toxoid gained less weight than pigs exposed only to adjuvant. Sera were collected from the pigs 28 days postinjection, and those that had been injected with the toxoid developed a neutralizing antibody titer that ranged from 1:128 to 1:512. Sera collected from the control group had no detectable neutralizing activity. Because weight gain in pigs is an indicator of general health, it appears that the toxoid had an adverse effect upon the animals. Results of histopathological examinations showed that all pigs which received the toxoid exhibited vascular lesions typical of ED (12, 13) in the brain (data not shown). To further characterize the toxoid in an attempt to explain the deleterious effect on pigs, its enzymatic activity was measured in a cell-free system. A dose-response curve describing the enzymatic activities of the toxoid and native SLT-IIv is shown in FIG. 3. Although the toxoid was completely inactive on cells, the $ID_{50}$ of the toxoid was determined to be 2,500 ng (Table 2), which indicated that the toxin has residual enzymatic activity. The data collected from the toxoid study revealed that formaldehyde treatment of SLT-IIv did not result in a safe, effective vaccine, even though the preparation was devoid of cytotoxic activity. The study also established that neonatal pigs were capable of mounting a specific immune response to SLT-IIv toxoid.

Figure 4:
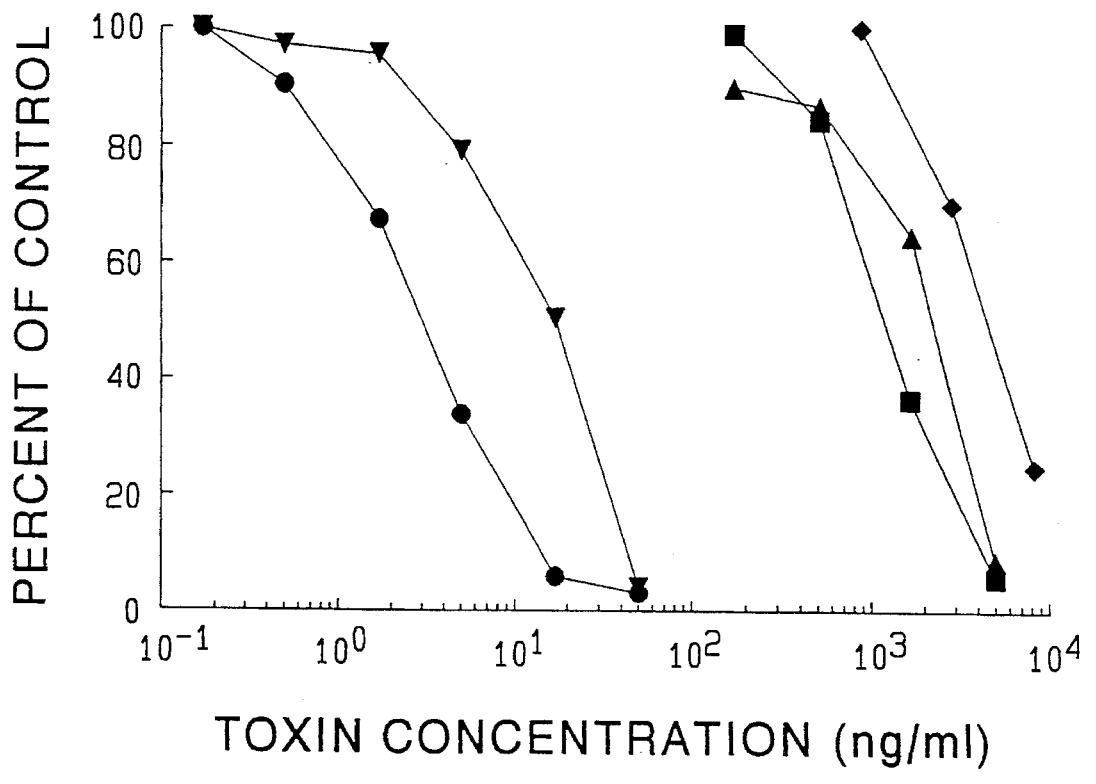
Figure 5A:
FIG. 5A and FIG. 5B show binding of SLT-IIv toxin and SLT-IIvE167Q to glycolipids separated by TLC. Crude sonicate of SLT-IIv (FIG. 5A) or SLT-IIvE167Q (FIG. 5B) was diluted 1:1,000 and incubated with TLC plates. Lanes 1, 1 microgram each of $Gb_3$, and $Gb_4$; lanes 2 HeLa cell glycolipids from 10 mg of cells; lanes 3 and 4, Vero cell glycolipids from 3 and 10 mg of cells, respectively.
Figure 5B:
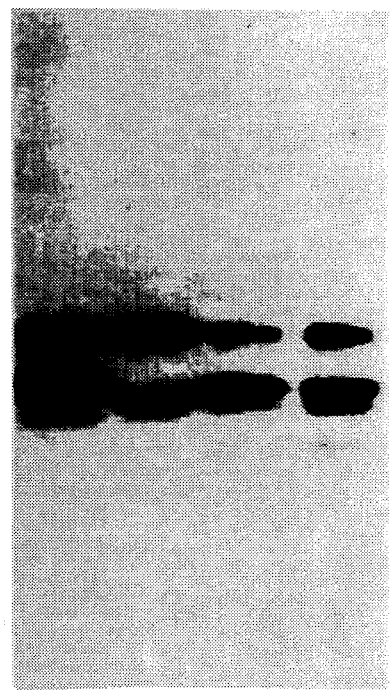
Figure 6:
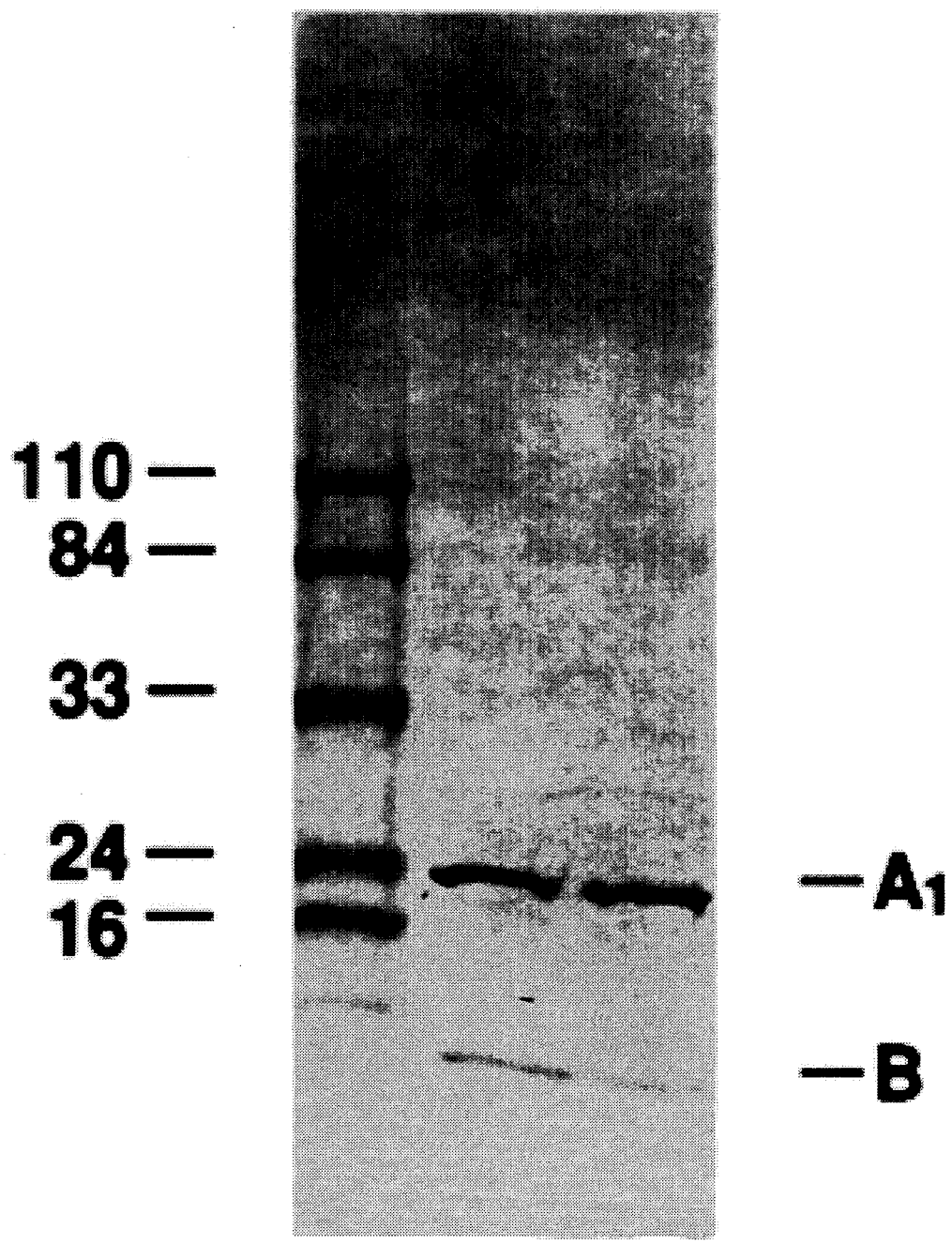
FIG. 6 shows immunoblot of SLT-IIv and SLT-IIvE167Q. Purified toxins (1 microgram) were visualized by electroblotting as described in the legend to FIG. 1. Lane 1, SLT-IIv; lane 2, SLT-IIvE167Q. The positions of the processed A, and B subunits of the toxins are indicated on the right. Prestained molecular weight standards and their molecular weights are shown in thousands on the left.

Identification of an Amino Acid Substitution in SLT-IIv that Drastically Reduces Enzymatic Activity To create a vaccine for ED with SLT-IIv which would not induce ED-like pathology when injected into neonatal pigs, oligonucleotide-specific site-directed mutants of SLT-IIv were constructed. On the basis of analysis of mutations in SLT-I and ricin (8, 9, 23), glutamate 167 and arginine 170 were targeted for mutation in SLT-IIv. These amino acids were changed to aspartate (E167D) and lysine (R170K), respectively. A double mutant (E1167D/R170K) that contained both changes was also made. These proteins were purified as described above, and the dose responsive curves that describe their enzymatic activities are shown in FIG. 4. A comparison of the enzymatic activities ($ID_{50}$) and cytotoxic activities (Vero $CD_{50}$) of the various mutants is shown in Table 2. A mutation in position 167 produced a more significant decrease in both cytotoxic and enzymatic activities than a mutation at position 170. When glutamic acid at position 167 was deleted, the subunits no longer associated as SLT-IIv holotoxin (data not shown). Enzymatic activity of the double mutant, SLT-IIvE167D/R170K, was approximately one-half that of SLT-IIvE167D, which indicated that a substitution of lysine for arginine at position 170 contributes minimally to the reduction in cytotoxic activity. All three mutants were predicted to be toxic for pigs because the minimum amount of native toxin that caused ED lesions had been reported to be several log units smaller than the dose estimated to produce an immune response. Therefore, a fourth A-subunit mutant, in which glutamine was substituted for glutamate at position 167, was created. The dose-responsive curve, which demonstrates that this substitution resulted in a further decrease in enzymatic activity, is shown in FIG. 4. The enzymatic activity ($ID_{50}$) and cytotoxic activity (Vero $CD_{50}$) for the E167Q mutant are shown in Table 2, and the values were significantly reduced in comparison with native toxin and SLT-IIvE167D values. To determine whether SLT-IIvE167Q assembled correctly into a bipartite toxin, this mutant was overlaid on glycolipids that were separated by TLC, as described above. The results, shown in FIG. 5, panel B demonstrate that the SLT-IIvE167Q mutant can simultaneously recognize glycolipids and an antibody directed against the A subunit and that its binding pattern to purified glycolipids and cell extracts appears identical to that of native toxin (FIG. 5, panel A). SLT-IIvE167Q was compared with native SLT-IIv by Western blot (immunoblot) analysis to examine its immunoreactivity. In an immunoblot, a polyclonal, monospecific antibody directed against SLT-IIv recognized both the mutant and native toxins (FIG. 6). Indeed, the molecular weights and immunoreactivities of the native and mutant toxins were indistinguishable.

Effects of Vaccinating Neonatal Pigs with SLT-IIvE167Q

The SLT-IIvE167Q mutant had low but detectable cytotoxic and enzymatic activities. This mutant was therefore used in a small study to ascertain that this low level of activity was not detrimental to pigs. Ten pigs from two litters born 2 days apart were divided into two groups. Five pigs were injected with adjuvant containing 50 micrograms of BSA, and five were injected with adjuvant containing 50 micrograms of SLT-IIvE167Q on day 17/19 and day 24/26 after birth. The pigs that received two 50micro grams doses of the mutant toxin gained weight comparably to control pigs (data not shown). On day 38/40, the pigs were sacrificed and samples from all of the animals were examined for histopathological symptoms. No ED lesions were found in either group (data not shown). Blood samples were obtained from the pigs on day 17/19 and on day 38/40 prior to sacrifice, and the sera were tested for the ability to neutralize SLT-IIv. The results indicate that the pigs had no previous exposure to SLT-IIv and that those vaccinated with the mutated toxin were able to mount an immune response and to develop a neutralizing antibody titer of 1:512 (data not shown). Sera from the control pigs had no detectable neutralizing activity (data not shown).

DISCUSSION

The results of the vaccine trial using formaldehyde-treated SLT-IIv in neonatal pigs highlight the drawbacks to using chemically inactivated toxins as vaccines. These disadvantages include the following: (i) the modifications undergone by the toxin are, in large part, unknown, (ii) formaldehyde treatment produces random modifications to proteins, and (iii) there is precedence for reversion back to an active form (24). For these reasons, a better vaccine candidate might be a toxin that has had its gene(s) modified such that it exhibits significantly reduced activity yet retains its antigenic structure.

The amino acids that were targeted for oligonucliotide-directed site-specific mutagenesis were selected on the basis of similarities among SLT-IIv, SLT-I, and ricin. Hovde et al. (8) implicated glutamate at position 167 as being important for enzymatic activity in SLT-I. Jackson et al. confirmed the importance of glutamate at position 167 in SLT-II (9). Schlossman et al. (23) made in analogous change in the ricin A chain, which also resulted in decreased enzymatic activity. Examination of the X-ray crystallographic structure of the ricin A chain led them to predict that arginine 180 (which corresponds to arginine 170 in SLT-IIv) interacts with glutamic acid 177 (which corresponds to glutamic acid 167 in SLT-IIv) and that a modification at position 180 would reduce catalytic activity. The results of similar changes in SLT-IIv are described in Table 2. As predicted, changes in position 167 had a dramatic effect on enzymatic activity. Altering the arginine at position 170, however, reduced enzymatic activity less than 10-fold (Table 2).

Replacing glutamate at position 167 with glutamine resulted in a significant reduction in enzymatic activity, and pigs injected with this preparation responded with a neutralizing titer of 1:512. The issue of vaccine safety, however, is not completely resolved, because this preparation retains a fraction of the activity of the native toxin. Boyd et al. (1) avoided the issue of residual toxicity by immunizing rabbits with SLT-I B subunit and obtained neutralizing sera. We believe that immunization with a mutated holotoxin is preferable to B subunit alone because such an immunogen should generate neutralizing antibodies directed against both the A and the B subunits of the toxin. Neutralization of enzymatic activity is particularly desirable for two reasons: cell death may result from exposure to very few toxin molecules, and even apparently insensitive cells may become sensitive when treated with a high concentration of toxin (unpublished results). Since the glycolipid receptor ($Gb_3$) for these toxins is present in high concentration on the surface of many cell types, neutralization of specific binding may not be sufficient to completely protect an animal that becomes colonized with virulent organisms.

The rationale behind selecting glutamine as a replacement for glutamate at position 167 of SLT-IIv was to maintain the native structure of the protein while altering the charge of the residue. There is a potential for deamination, however, which would result in a reversion of wild-type activity. Deamination would most likely occur at extreme pH or high temperature. It is unlikely that the putative vaccine will encounter either of these conditions. Nonetheless, we investigated the likelihood of deamination by exposing purified SLT-IIv and SLT-IIvE167Q to pH 7.0, 5.0, or 3.0 at 37 or 50° C. for 1 h. These preparations were then assayed for cytotoxic activity. Although the native toxin lost 4 logs of activity at pH 3 and 50° C., the cytotoxic activity of the mutant toxin was undetectable under all conditions (data not shown). Furthermore, histological examination from tissues of pigs that were injected with 100 (mu)g of SLT-IIvE167Q did not exhibit ED lesions (data not shown). These observations indicate that no detectable reversion of toxicity occurs in vitro or in vivo.

SUMMARY

Edema disease (ED) of weanling pigs is caused by an infection with *Escherichia coli* that produces Shiga-like toxin II variant (SLT-IIv). Pathology identical to that caused by ED can be duplicated in pigs that are injected with <10 ng of purified SLT-IIv per kg of body weight. Therefore, SLT-IIv was mutated to create an immunoreactive form of the toxin that was significantly reduced in enzymatic activity.

Initially, purified SLT-IIv was treated with formaldehyde which abrogated cytotoxic activity. Pigs were vaccinated with the toxoid (100 micrograms) to determine whether a toxoid was a viable vaccine candidate and whether young pigs were capable of mounting an immune response. Although the pigs developed a neutralizing antibody titer (1:128 to 1:512) 28 days postinjection, they also lost weight and developed ED lesions. The deleterious effect of the toxoid appeared to result from residual enzymatic activity or a reversion to a toxic form.

An alternative method, site-directed mutagenesis, was employed to consistently reduce the enzymatic activity of SLT-IIv. Glutamate at position 167 of the mature A subunit was replaced by aspartate (E167D), and arginine at position 170 was replaced by lysine (R170K). These mutations reduced cytotoxic activity $10^4$-fold and 10-fold, respectively, while the enzymatic activities were decreased 400-fold and 5-fold, respectively. The activity of a toxin that contained both mutations (SLT-IIvE167D/R170K) closely resembled that of SLT-IIvE167D. When position 167 was replaced by glutamine (E167Q), the cytotoxic activity and enzymatic activity decreased drastically, $10^6$-fold and 1,500-fold, respectively. Pigs that were vaccinated with purified, mutant toxin designated SLT-IIvE167Q developed a neutralizing antibody titer of 1:512 21 days postinjection, and their tissues were free of ED lesions. These data suggest that SLT-IIvE167Q may represent an effective vaccine against ED.

TABLE 1

Weights of pigs injected with adjuvant or SLT-IIv toxoid[a]

| Prepn injected | Avg wt (lbs[b]) ± SD at: | | |
|---|---|---|---|
| | Day 22 | Day 29 | Day 36 |
| Adjuvant | 11.1 ± 1.95 | 12.9 ± 2.14 | 14.1 ± 2.84 |
| SLT-IIv toxoid | 10.1 ± 1.69 | 9.7 ± 1.64 | 9.7 ± 1.72 |

TABLE 1-continued

Weights of pigs injected with adjuvant or SLT-IIv toxoid[a]

| Prepn injected | Avg wt (lbs[b]) ± SD at: | | |
|---|---|---|---|
| | Day 22 | Day 29 | Day 36 |
| pc | <0.01 | <0.001 | <0.001 |

[a]Pigs (34 per group) were injected with Al(OH)$_3$ adjuvant in PBS or adjuvant containing 50 micrograms of SLT-IIv toxoid in PBS on days 7 and 14 of life.
[b]1 lb = ca. 0.454 kg.
[c]Probability values were determined with a two-tailed Student's $t$ test.

TABLE 2

Cytotoxic and enzymatic activities of wild-type and mutant SLT-IIv toxins

| Toxin prepn[a] | Cytotoxic activity[b] (pg) | Enzymatic activity[c] (ng/ml) |
|---|---|---|
| SLT-IIv | 0.01 | 3.1 |
| SLT-IIv toxoid | ND | 2,500 |
| SLT-IIvE167D | 100 | 1,200 |
| SLT-IIvR170K | 0.1 | 17 |
| SLT-IIvE167D/R170K | 100 | 2,250 |
| SLT-IIvE167Q | 10,000 | 4,600 |

[a]SLT-IIv toxin or toxoid was purified as described in Materials and Methods.
[b]Purified preparations were incubated with Vero cells for 48 h at 37° C. The titer was determined to be the amount of toxin which was lethal for 50% of the cells. ND, no detectable cytotoxic activity.
[c]Enzymatic activity was quantitated by inhibition of in vitro protein translation as described in the text. The ID$_{50}$ was determined to be the concentration of toxin which inhibited incorporation of $^{35}$S-methionine by 50%.

REFERENCES

1. Boyd, et al., 1991. *Infect. Immun.* 59:750–757.
2. Clugston, et al., 1974. *Can. J. Comp. Med.* 38:34–43.
3. Endo, et al., 1988. *Eur. J. Biochem.* 171:45–50.
4. Federal Register, 1986. Recombinant DNA research guidelines, appendix F-IV-H. *Fed. Regist.* 51:16972.
5. Frankel, et al., 1989. *Mol. Cell. Biol.* 9:415–420.
6. Frankel, et al., 1990. *Mol. Cell. Biol.* 10:6257–6263.
7. Gentry, et al., 1980. *J. Clin. Microbiol.* 12:361–366.
8. Hovde, 1988. *Proc. Natl. Acad. Sci. USA* 85:2568–2572.
9. Jackson, et al., 1990. *J. Bacteriol* 172:3346–3350.
10. Karmall, et al., 1989. *Clin. Microbiol. Rev.* 2:15–38.
11. Karmall, et al., 1985. *J. Infect. Dis.* 151:775–782.
12. Kausche. et al., *Am. J. Vet. Res.*, in press.
13. Laemmli, 1970. *Nature (London)* 227:680–685.
14. MacLeod, et al., 1991. *Vet. Pathol.* 28:66–73.
15. Marques, et al., 1986. *J. Infect. Dis.* 154:338–341.
16. Marques, et al., 1987. *FEMS Microbiol. Lett.* 44:33–38.
17. Mata, et al., 1970. *J. Infect. Dis.* 122:170–180.
18. Morrison, et al., 1985. *Am. J. Clin. Pathol.* 86:108–112.
19. National Institutes of Health, 1985. Guide for the care and use of laboratory animals. National Institutes of Health publication no. 85–23. National Institutes of Health, Bethesda, Md.
20. O'Brien, et al., 1987. *Microbiol. Rev.* 51:206–220.

21. O'Brien, et al., 1983. *Infect. Immun.* 40:675–683.

22. Samuel, et al., 1990. *Infect. Immun.* 58:611–618.

23. Schlossman, et al., 1989. *Mol. Cell. Biol.* 9:5012–5021.

24. Starsaeter, et al., 1988. *Pediatr. Infect. Dis. J.* 7:637–645.

25. Towbin, et al., 1979. *Proc. Natl. Acad. Sci. USA* 76:4350–354.

26. Weinstein, et al., 1988. *J. Bacteriology* 170:4223–4230.

---

We claim:

1. An immunogenic mutant Shiga-Like Toxin II variant (SLT-IIv) holotoxin comprising SEQ ID NO:2, which is a mutant A subunit of the SLT-IIv holotoxin, wherein said mutant A subunit differs from the native A subunit of the SLT-IIv holotoxin in having a glutamine at residue 167 and SEQ ID NO:3, which is the B subunit of the SLT-IIv holotoxin; and wherein the enzymatic activity of said mutant SLT-IIv holotoxin is reduced by at least 750-fold and the cytotoxicity is reduced by at least 10,000-fold compared to the native SLT-IIv holotoxin.

2. The immunogenic mutant SLT-IIv holotoxin of claim 1 wherein said immunogenic mutant SLT-IIv holotoxin is essentially purified.

3. An immunogenic polypeptide comprising SEQ ID NO:1 or SEQ ID NO:2, which is a mutant A subunit of Shiga-Like Toxin II variant (SLT-IIv) holotoxin, wherein said mutant A subunit differs from the native A subunit of SLT-IIv holotoxin in having a glutamine at residue 167 and wherein the enzymatic activity of said mutant A subunit is reduced by at least 750-fold and the cytotoxicity of said polypeptide when complexed with the native subunit B of SLT-IIv holotoxin is reduced by at least 10,000-fold compared to the native A subunit when complexed with the native subunit B of the SLT-IIv holotoxin.

4. A vaccine for inducing an immune response in an animal host to bacteria that causes edema disease of swine comprising an immunologically effective amount of the immunogenic mutant Shiga-Like Toxin II variant holotoxin of claim 1 or the immunogenic polypeptide of claim 3 in a pharmaceutically acceptable carrier.

5. A method of inducing an immune response in an animal host to bacteria that cause edema disease of swine comprising administering an immunologically effective amount of the immunogenic mutant Shiga-Like Toxin II variant holotoxin of claim 1 to said host.

6. The method of claim 5 wherein said animal host is a pig.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 319 amino acids
        ( B ) TYPE: amino acid
        ( C ) STRANDEDNESS: unknown
        ( D ) TOPOLOGY: unknown ( i i ) MOLECULE TYPE: protein ( i x ) FEATURE:
        ( A ) NAME/KEY: signal sequence
        ( B ) LOCATION: -22 to -1

( x i ) SEQUENCE DESCRIPTION: SEQ ID NO:1:

```
Met  Lys  Cys  Ile  Leu  Leu  Lys  Trp  Ile  Leu  Cys  Leu  Leu  Leu  Gly  Phe
     -20                      -15                      -10

Ser  Ser  Val  Ser  Tyr  Ser  Gln  Glu  Phe  Thr  Ile  Asp  Phe  Ser  Thr  Gln
     -5                       1                        5                       10

Gln  Ser  Tyr  Val  Ser  Ser  Leu  Asn  Ser  Ile  Arg  Thr  Ala  Ile  Ser  Thr
                    15                       20                       25

Pro  Leu  Glu  His  Ile  Ser  Gln  Gly  Ala  Thr  Ser  Val  Ser  Val  Ile  Asn
               30                       35                       40

His  Thr  Pro  Pro  Gly  Ser  Tyr  Ile  Ser  Val  Gly  Ile  Arg  Gly  Leu  Asp
               45                       50                       55

Val  Tyr  Gln  Glu  Arg  Phe  Asp  His  Leu  Arg  Leu  Ile  Ile  Glu  Arg  Asn
     60                       65                       70

Asn  Leu  Tyr  Val  Ala  Gly  Phe  Val  Asn  Thr  Thr  Thr  Asn  Thr  Phe  Tyr
75                       80                       85                            90

Arg  Phe  Ser  Asp  Phe  Ala  His  Ile  Ser  Leu  Pro  Gly  Val  Thr  Thr  Ile
                    95                       100                      105

Ser  Met  Thr  Thr  Asp  Ser  Ser  Tyr  Thr  Thr  Leu  Gln  Arg  Val  Ala  Ala
               110                      115                      120

Leu  Glu  Arg  Ser  Gly  Met  Gln  Ile  Ser  Arg  His  Ser  Leu  Val  Ser  Ser
          125                      130                      135

Tyr  Leu  Ala  Leu  Met  Glu  Phe  Ser  Gly  Asn  Thr  Met  Thr  Arg  Asp  Ala
     140                      145                      150

Ser  Arg  Ala  Val  Leu  Arg  Phe  Val  Thr  Val  Thr  Ala  Gln  Ala  Leu  Arg
155                      160                      165                           170

Phe  Arg  Gln  Ile  Gln  Arg  Glu  Phe  Arg  Leu  Ala  Leu  Ser  Glu  Thr  Ala
                    175                      180                      185

Pro  Val  Tyr  Thr  Met  Thr  Pro  Glu  Asp  Val  Asp  Leu  Thr  Leu  Asn  Trp
               190                      195                      200

Gly  Arg  Ile  Ser  Asn  Val  Leu  Pro  Glu  Tyr  Arg  Gly  Glu  Ala  Gly  Val
          205                      210                      215

Arg  Val  Gly  Arg  Ile  Ser  Phe  Asn  Asn  Ile  Ser  Ala  Ile  Leu  Gly  Thr
     220                      225                      230
```

```
Val  Ala  Val  Ile  Leu  Asn  Cys  His  His  Gln  Gly  Ala  Arg  Ser  Val  Arg
235                      240                     245                          250

Ala  Val  Asn  Glu  Glu  Ser  Gln  Pro  Glu  Cys  Gln  Ile  Thr  Gly  Asp  Arg
                         255                     260                     265

Pro  Val  Ile  Lys  Ile  Asn  Asn  Thr  Leu  Trp  Glu  Ser  Asn  Thr  Ala  Ala
               270                      275                          280

Ala  Phe  Leu  Asn  Arg  Lys  Ser  Gln  Ser  Leu  Tyr  Thr  Thr  Gly  Glu
          285                      290                          295
```

( 2 ) INFORMATION FOR SEQ ID NO:2:

( i ) SEQUENCE CHARACTERISTICS:
        ( A ) LENGTH: 297 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:2:

```
Gln  Glu  Phe  Thr  Ile  Asp  Phe  Ser  Thr  Gln  Gln  Ser  Tyr  Val  Ser  Ser
1                   5                        10                          15

Leu  Asn  Ser  Ile  Arg  Thr  Ala  Ile  Ser  Thr  Pro  Leu  Glu  His  Ile  Ser
               20                      25                     30

Gln  Gly  Ala  Thr  Ser  Val  Ser  Val  Ile  Asn  His  Thr  Pro  Pro  Gly  Ser
          35                      40                          45

Tyr  Ile  Ser  Val  Gly  Ile  Arg  Gly  Leu  Asp  Val  Tyr  Gln  Glu  Arg  Phe
     50                      55                     60

Asp  His  Leu  Arg  Leu  Ile  Ile  Glu  Arg  Asn  Asn  Leu  Tyr  Val  Ala  Gly
65                       70                     75                           80

Phe  Val  Asn  Thr  Thr  Asn  Thr  Phe  Tyr  Arg  Phe  Ser  Asp  Phe  Ala
                    85                      90                          95

His  Ile  Ser  Leu  Pro  Gly  Val  Thr  Thr  Ile  Ser  Met  Thr  Thr  Asp  Ser
               100                     105                         110

Ser  Tyr  Thr  Thr  Leu  Gln  Arg  Val  Ala  Ala  Leu  Glu  Arg  Ser  Gly  Met
               115                     120                         125

Gln  Ile  Ser  Arg  His  Ser  Leu  Val  Ser  Ser  Tyr  Leu  Ala  Leu  Met  Glu
     130                     135                          140

Phe  Ser  Gly  Asn  Thr  Met  Thr  Arg  Asp  Ala  Ser  Arg  Ala  Val  Leu  Arg
145                      150                     155                          160

Phe  Val  Thr  Val  Thr  Ala  Gln  Ala  Leu  Arg  Phe  Arg  Gln  Ile  Gln  Arg
                    165                     170                         175

Glu  Phe  Arg  Leu  Ala  Leu  Ser  Glu  Thr  Ala  Pro  Val  Tyr  Thr  Met  Thr
               180                     185                         190

Pro  Glu  Asp  Val  Asp  Leu  Thr  Leu  Asn  Trp  Gly  Arg  Ile  Ser  Asn  Val
          195                     200                          205

Leu  Pro  Glu  Tyr  Arg  Gly  Glu  Ala  Gly  Val  Arg  Val  Gly  Arg  Ile  Ser
     210                     215                          220

Phe  Asn  Asn  Ile  Ser  Ala  Ile  Leu  Gly  Thr  Val  Ala  Val  Ile  Leu  Asn
225                      230                     235                          240

Cys  His  His  Gln  Gly  Ala  Arg  Ser  Val  Arg  Ala  Val  Asn  Glu  Glu  Ser
                    245                     250                         255

Gln  Pro  Glu  Cys  Gln  Ile  Thr  Gly  Asp  Arg  Pro  Val  Ile  Lys  Ile  Asn
               260                     265                         270

Asn  Thr  Leu  Trp  Glu  Ser  Asn  Thr  Ala  Ala  Ala  Phe  Leu  Asn  Arg  Lys
          275                     280                          285
```

Ser Gln Ser Leu Tyr Thr Thr Gly Glu
290                 295

(2) INFORMATION FOR SEQ ID NO:3:

(i) SEQUENCE CHARACTERISTICS:
    (A) LENGTH: 68 amino acids
    (B) TYPE: amino acid
    (C) STRANDEDNESS: unknown
    (D) TOPOLOGY: unknown (ii) MOLECULE TYPE: protein (xi) SEQUENCE DESCRIPTION: SEQ ID NO:3:

Ala Asp Cys Ala Lys Gly Lys Ile Glu Phe Ser Lys Tyr Asn Glu Asp
1               5               10                  15

Asn Thr Phe Thr Val Lys Val Ser Gly Arg Glu Tyr Trp Thr Asn Arg
            20              25                  30

Trp Asn Leu Gln Pro Leu Leu Gln Ser Ala Gln Leu Thr Gly Met Thr
        35              40              45

Val Thr Ile Ile Ser Asn Thr Cys Ser Ser Gly Ser Gly Phe Ala Gln
    50              55                  60

Val Lys Phe Asn
65